(12) United States Patent
Kimball et al.

(10) Patent No.: US 10,388,142 B2
(45) Date of Patent: *Aug. 20, 2019

(54) METHODS AND SYSTEMS FOR PROVIDING BATTERY FEEDBACK TO PATIENT

(71) Applicant: TC1 LLC, St. Paul, MN (US)

(72) Inventors: Brian Kimball, Medford, MA (US);
Charles Dague, Windham, NH (US);
W. Kevin Wu, Carlisle, MA (US)

(73) Assignee: TC1 LLC, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/150,145

(22) Filed: Oct. 2, 2018

(65) Prior Publication Data

US 2019/0035254 A1  Jan. 31, 2019

Related U.S. Application Data

(63) Continuation of application No. 15/697,305, filed on Sep. 6, 2017, now Pat. No. 10,115,290, which is a continuation of application No. 14/687,746, filed on Apr. 15, 2015, now Pat. No. 9,786,150.

(60) Provisional application No. 61/979,845, filed on Apr. 15, 2014.

(51) Int. Cl.
*G08B 21/18* (2006.01)
*A61M 1/10* (2006.01)
*A61M 1/12* (2006.01)

(52) U.S. Cl.
CPC ......... *G08B 21/182* (2013.01); *A61M 1/1086* (2013.01); *A61M 1/122* (2014.02); *A61M 1/127* (2013.01)

(58) Field of Classification Search
CPC ..... A61M 1/10; G08B 21/182; G08B 29/181; Y02E 60/12; H01M 10/48; G01R 31/3648; H02J 7/0047
See application file for complete search history.

(56) References Cited

U.S. PATENT DOCUMENTS

| | | | |
|---|---|---|---|
| 5,370,668 A | 12/1994 | Shelton et al. | |
| 5,695,471 A | 12/1997 | Wampler | |
| 5,708,346 A | 1/1998 | Schob | |
| 5,725,357 A | 3/1998 | Nakazeki et al. | |
| 5,888,242 A | 3/1999 | Antaki et al. | |
| 6,053,705 A | 4/2000 | Schob et al. | |

(Continued)

FOREIGN PATENT DOCUMENTS

| | | | |
|---|---|---|---|
| EP | 1812094 A2 | 8/2007 | |
| WO | 0222200 A1 | 3/2002 | |

(Continued)

*Primary Examiner* — Sisay Yacob
(74) *Attorney, Agent, or Firm* — Kilpatrick Townsend and Stockton LLP

(57) ABSTRACT

A method for outputting a combined power source alarm for an implantable blood pump includes determining a status for each of first and second power sources of the blood pump. A combined power source alarm based on the statuses of the first and second power sources is outputted. A method for generating an alarm based on fault detections in a mechanically assisted circulation system includes processing a series of fault detection indications to classify a fault as active or inactive. An alarm is generated if the fault is active for more than a predetermined amount of time.

20 Claims, 8 Drawing Sheets

(56) References Cited

U.S. PATENT DOCUMENTS

| | | |
|---|---|---|
| 6,071,093 A | 6/2000 | Hart |
| 6,100,618 A | 8/2000 | Schoeb et al. |
| 6,116,862 A | 9/2000 | Rau et al. |
| 6,146,325 A | 11/2000 | Lewis et al. |
| 6,149,683 A | 11/2000 | Lancisi et al. |
| 6,186,665 B1 | 2/2001 | Maher et al. |
| 6,222,290 B1 | 4/2001 | Schob et al. |
| 6,234,772 B1 | 5/2001 | Wampler et al. |
| 6,249,067 B1 | 6/2001 | Schob et al. |
| 6,264,635 B1 | 7/2001 | Wampler et al. |
| 6,278,251 B1 | 8/2001 | Schob |
| 6,351,048 B1 | 2/2002 | Schob et al. |
| 6,355,998 B1 | 3/2002 | Schob et al. |
| 6,395,027 B1 | 5/2002 | Snyder |
| 6,468,041 B2 | 10/2002 | Ozaki |
| 6,575,717 B2 | 6/2003 | Ozaki et al. |
| 6,589,030 B2 | 7/2003 | Ozaki |
| 6,605,032 B2 | 8/2003 | Benkowski et al. |
| 6,626,644 B2 | 9/2003 | Ozaki |
| 6,634,224 B1 | 10/2003 | Schob et al. |
| 6,671,552 B2 | 12/2003 | Merritt et al. |
| 6,688,861 B2 | 2/2004 | Wampler |
| 6,707,200 B2 | 3/2004 | Carroll et al. |
| 6,817,836 B2 | 11/2004 | Nose et al. |
| 6,879,074 B2 | 4/2005 | Amrhein et al. |
| 6,949,066 B2 | 9/2005 | Bearnson et al. |
| 6,991,595 B2 | 1/2006 | Burke et al. |
| 7,112,903 B1 | 9/2006 | Schob |
| 7,138,776 B1 | 11/2006 | Gauthier et al. |
| 7,150,711 B2 | 12/2006 | Nusser et al. |
| 7,229,474 B2 | 6/2007 | Hoffmann et al. |
| 7,239,098 B2 | 7/2007 | Masino |
| 7,284,956 B2 | 10/2007 | Nose et al. |
| 7,462,019 B1 | 12/2008 | Allarie et al. |
| 7,497,116 B2 | 3/2009 | Miyakoshi et al. |
| 7,511,443 B2 | 3/2009 | Townsend et al. |
| 7,591,777 B2 | 9/2009 | Larose |
| 7,645,225 B2 | 1/2010 | Medvedev et al. |
| 7,699,586 B2 | 4/2010 | LaRose et al. |
| 7,699,588 B2 | 4/2010 | Mendler |
| 7,854,631 B2 | 12/2010 | Townsendl et al. |
| 7,861,582 B2 | 1/2011 | Miyakoshi et al. |
| 7,887,479 B2 | 2/2011 | Larose et al. |
| 7,945,327 B2 | 5/2011 | Gandhi et al. |
| 7,951,062 B2 | 5/2011 | Morello |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,152,493 B2 | 4/2012 | LaRose et al. |
| 8,157,720 B2 * | 4/2012 | Marseille ............ A61M 1/1086 600/16 |
| 8,303,482 B2 | 11/2012 | Schima et al. |
| 8,323,174 B2 | 12/2012 | Jeevanandam et al. |
| 8,382,830 B2 | 2/2013 | Maher et al. |
| 8,419,789 B2 | 4/2013 | Shu et al. |
| 8,449,444 B2 | 5/2013 | Poirier |
| 8,454,549 B2 | 6/2013 | Zafirelis et al. |
| 8,506,470 B2 | 8/2013 | Larose et al. |
| 8,506,471 B2 | 8/2013 | Bourque |
| 8,517,699 B2 | 8/2013 | Horvath |
| 8,556,795 B2 | 10/2013 | Bolyard et al. |
| 8,562,508 B2 | 10/2013 | Dague et al. |
| 8,597,350 B2 * | 12/2013 | Rudser ................ A61M 1/1001 623/3.1 |
| 8,608,635 B2 | 12/2013 | Yomtov et al. |
| 8,612,167 B2 | 12/2013 | Schmidt et al. |
| 8,652,024 B1 | 2/2014 | Yanai et al. |
| 8,657,733 B2 | 2/2014 | Ayre et al. |
| 8,668,473 B2 | 3/2014 | Larose et al. |
| 8,764,621 B2 | 7/2014 | Badstibner et al. |
| 8,766,788 B2 * | 7/2014 | D'Ambrosio .......... A61B 5/686 340/539.11 |
| 8,870,739 B2 | 10/2014 | Larose et al. |
| 8,882,477 B2 | 11/2014 | Fritz, IV et al. |
| 8,956,275 B2 | 2/2015 | Bolyard et al. |
| 2005/0071001 A1 | 3/2005 | Jarvik |
| 2007/0078293 A1 | 4/2007 | Shambaugh, Jr. et al. |
| 2008/0021394 A1 | 1/2008 | Larose et al. |
| 2009/0203957 A1 | 8/2009 | Larose et al. |
| 2010/0130809 A1 | 5/2010 | Morello |
| 2010/0241223 A1 | 9/2010 | Lee et al. |
| 2010/0305692 A1 * | 12/2010 | Thomas ................ A61M 1/10 623/3.1 |
| 2010/0327687 A1 | 12/2010 | Iannello et al. |
| 2011/0071336 A1 | 3/2011 | Yomtov et al. |
| 2011/0071337 A1 | 3/2011 | Thompson et al. |
| 2011/0237863 A1 | 9/2011 | Ricci et al. |
| 2011/0313237 A1 | 12/2011 | Miyakoshi et al. |
| 2012/0046514 A1 | 2/2012 | Bourque |
| 2012/0095281 A1 | 4/2012 | Reichenbach et al. |
| 2012/0154143 A1 * | 6/2012 | D'Ambrosio .......... A61B 5/686 340/539.11 |
| 2012/0226097 A1 | 9/2012 | Smith et al. |
| 2012/0245681 A1 | 9/2012 | Casas et al. |
| 2012/0277520 A1 | 11/2012 | Duncan et al. |
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |
| 2013/0331934 A1 | 12/2013 | Kabir et al. |
| 2014/0100413 A1 | 4/2014 | Casas et al. |
| 2014/0194985 A1 | 7/2014 | Vadala, Jr. |
| 2014/0275723 A1 | 9/2014 | Fritz et al. |
| 2014/0303426 A1 | 10/2014 | Kerkhoffs et al. |
| 2014/0357937 A1 | 12/2014 | Reyes et al. |
| 2015/0051438 A1 | 2/2015 | Taskin |
| 2015/0294550 A1 | 10/2015 | Kimball et al. |
| 2017/0365154 A1 | 12/2017 | Kimball et al. |

FOREIGN PATENT DOCUMENTS

| | | | |
|---|---|---|---|
| WO | 2008154387 A1 | 12/2008 |
| WO | 2012071065 A1 | 5/2012 |
| WO | 2012087819 A1 | 6/2012 |

* cited by examiner

FIG. 10

|  | | BLACK CABLE STATUS | | | | |
|---|---|---|---|---|---|---|
|  | | Power Cable Disconnected | Unknown Status | Red R.S.O.C. Status | Yellow R.S.O.C. Status | Green R.S.O.C. Status |
| WHITE CABLE STATUS | | No External Power + Power Cable Disconnect | Power Cable Disconnect + Low Power Hazard | Power Cable Disconnect + Low Power Hazard | Power Cable Disconnect + Low Power Hazard | Power Cable Disconnect + Low Power Advisory |
| | | Power Cable Disconnect + Low Power Hazard | Power Cable Disconnect + Low Power Hazard | Power Cable Disconnect + Low Power Hazard | Power Cable Disconnect + Low Power Hazard | Power Cable Disconnect + Low Power Advisory |
| | | Power Cable Disconnect + Low Power Hazard | Power Cable Disconnect + Low Power Hazard | Low Power Hazard | Low Power Hazard | Low Power Advisory |
| | | Power Cable Disconnect + Low Power Hazard | Power Cable Disconnect + Low Power Hazard | Low Power Hazard | Low Power Advisory | Low Power Advisory |
| | | Power Cable Disconnect + Low Power Hazard | Power Cable Disconnect + Low Power Advisory | Low Power Advisory | Low Power Advisory | No Alarm |

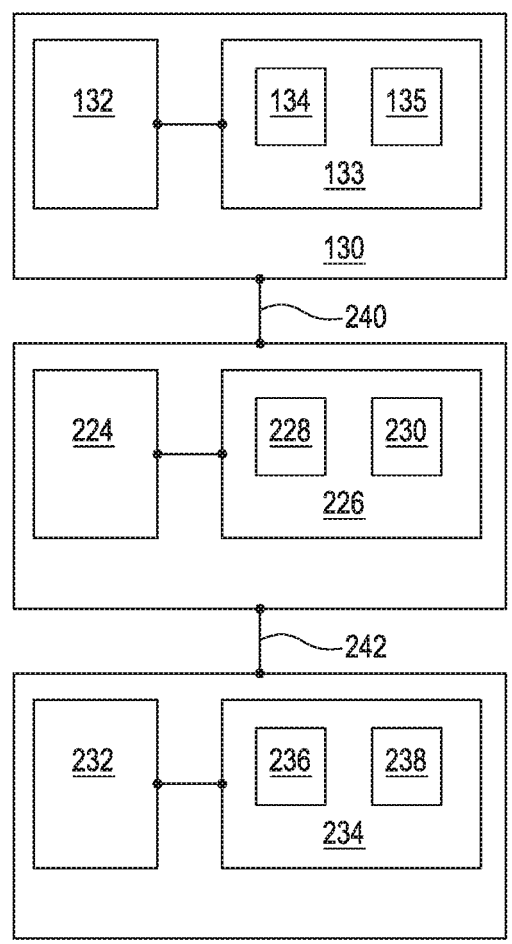

METHODS AND SYSTEMS FOR PROVIDING BATTERY FEEDBACK TO PATIENT

CROSS-REFERENCES TO RELATED APPLICATIONS

This application is a continuation of U.S. patent application Ser. No. 15/697,305, filed Sep. 6, 2017, which is a continuation of U.S. patent application Ser. No. 14/687,746, filed Apr. 15, 2015, now U.S. Pat. No. 9,786,150, issued on Oct. 10, 2017, which claims the benefit of U.S. Provisional Application No. 61/979,845, filed Apr. 15, 2014, the contents of which are hereby incorporated by reference in their entirety for all purposes.

BACKGROUND

This application relates generally to mechanically assisted circulation (MAC) systems, and more specifically relates to improved methods and systems for generating alarms based on fault detections in a MAC system. Such alarms can relate to an implantable blood pump of an MAC system as well as to power sources for the blood pump.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

In view of the critical nature of the support provided by a MAC system, close monitoring of the MAC system may be used to detect faults within the MAC system that, if not suitably addressed in time, may result in failure of the MAC system that may endanger the life of the patient. For example, monitoring of an implanted blood pump may detect a fault condition that is likely to worsen over time, thereby requiring corrective action to be taken before the fault condition becomes critical. As another example, fault conditions within a power supply system, such as low power states and/or disconnects may be detected and communicated to the patient so that the patient can take appropriate action to avoid a critical loss of power supply to the MAC system.

Close monitoring, however, can result in the detection of transient faults, which if communicated to the patient can result in the patient being subjected to undue stress. Such communication of transient faults to the patient may even result in the patient failing to take necessary action when subsequently informed of an actual critical fault.

Moreover, power is often supplied to an implantable blood pump via redundant power sources so as to decrease the probability of power interruption to the blood pump. The use of multiple power sources, however, increases the number of power source component faults that may occur, thereby increasing the number of potential faults for a patient to contend with.

Accordingly, improved approaches for monitoring MAC systems such that communication with the patient is undertaken that is appropriate in view of the condition of the MAC system are desirable.

BRIEF SUMMARY

Improved methods and systems for generating alarms based on fault detections are provided. Fault detections are processed to ensure that a fault is consistently occurring before a fault is considered active. Once a fault is considered active, the active fault can then be assessed to see of the fault is active for a predetermined amount of time before communicating the fault (e.g., false positive) to the patient. Accordingly, subjecting a patient to an alarm based on a transient fault can be suppressed, thereby avoiding subjecting the patient to undue stress.

Thus, in one aspect, a method is provided of generating an alarm based on fault detections in a MAC system. The method includes receiving a series of indications from a subsystem of the MAC system indicative of whether a fault condition is being detected or not detected. If each of a first subseries of the series of indications at the end of the series of indications each indicate a detection of the fault condition and the number of the first subseries equals or exceeds a predetermined set soaking number for the fault, the fault is indicated as being active. If each of a second subseries of the series of indications at the end of the series of indications each indicate a non-detection of the fault condition and the number of the second subseries equals or exceeds a predetermined clear soaking number for the fault, the fault is indicated as being inactive. An alarm for the fault is generated when the fault is active for at least a predetermined amount of time.

Any suitable number(s) for the set soaking number and clear soaking number can be used. For example, for any particular fault, the set soaking number can be selected to be any number from one to ten. In many embodiments, the clear soaking number is selected to be any suitable number, for example, any number from one to three. The larger the set soaking number, the greater the number of fault detection indications required before the fault is considered active. The smaller the clear soaking number, the faster the fault is reconsidered as inactive instead of active.

Any relationship between the set soaking number and the clear soaking number can be used. For example, the clear soaking number can be greater than the set soaking number. The clear soaking number can be equal to the set soaking number. And the clear soaking number can be less than the set soaking number.

The predetermined amount of time can be any suitable amount of time. For example, the predetermined amount of time can be up to and equal to fifteen seconds.

In many embodiments, the MAC system includes an implantable blood pump and the fault relates to the blood pump. For example, the fault can be with respect to one or more power sources for the implantable blood pump. As another example, the fault can be with respect to the implantable blood pump.

Additionally, improved methods and systems for generating a power source status for an implantable blood pump are provided. Often, a power system for an implantable blood pump includes redundant power sources. The improved methods and systems disclosed herein generate a combined power source status for the redundant power sources, thereby reducing the extent of the status (e.g., number of status indications) that may be communicated to the patient. Additionally, the combined power source status accounts for the individual statuses of the redundant power sources, thereby avoiding potential patient stress and/or patient uncertainty as to the appropriate action to take when confronted with numerous individual statuses of the redundant power sources.

Thus, in another aspect, a computer implemented method of outputting a combined power source alarm for an implantable blood pump is provided. The method includes determining a status of a first power source for the implantable blood pump assembly. The status of a second power source for the implantable blood pump assembly is determined, wherein the second power source is different from the first power source. A combined power source alarm is outputted that is based on the statuses of the first and second power sources. In many embodiments, the method is carried out by a control unit for the implantable blood pump.

In many embodiments, a status for each of the first and second power sources is determined. For example, the determined status of each of the first and second power sources can be selected from: (a) a first status indicative of a relative state of charge being between a first threshold and a full state of charge for the respective power source; (b) a second status indicative of a relative state of charge being between the first threshold and a second threshold lower than the first threshold; (c) a third status indicative of a relative state of charge being below the second threshold; (d) a fourth status indicative of the power source being unknown; and (e) a fifth status indicative of a power cable disconnect.

Outputting the combined power source alarm can include displaying a low power advisory alarm. For example, the low power advisory alarm can be displayed if: (a) the status of at least one of the first and second power sources is the second status and the status of each of the first and second power sources is the first or second status, or (b) the status of one of the first and second power sources is the first status and the status of the other one of the first and second power sources is the third status. Displaying the low power advisory alarm can include repeatedly flashing an indicator light for at least one second on followed by at least one second off. The indicator light can be yellow and shaped in any suitable form (e.g., diamond shaped, in the form of a battery or a battery symbol). An audio beep can be repeatedly sounded during the low power advisory alarm once every four or more seconds or until silenced via a user selection.

Outputting the combined power source alarm can include displaying a low power hazard alarm. For example, the low power hazard alarm can be displayed if the status of at least one of the first and second power sources is the third status and the status of each of the first and second power sources is the second or third status. Displaying the low power hazard alarm can include repeatedly flashing an indicator light for at least 0.25 seconds on followed by at least 0.25 seconds off. The indicator light can be red and shaped in any suitable form (e.g., diamond shaped, in the form of a battery or a battery symbol). A continuous audio tone can be sounded for a length of the low power hazard alarm or until the continuous audio tone is silenced via a user selection. The continuous audio tone can be sounded a second time after being silenced via the user selection if the low power hazard alarm persists longer than a predetermined amount of time after the audio tone is silenced.

Outputting the combined power source alarm can include displaying a power cable disconnect and low power advisory alarm. For example, the power cable disconnect and low power advisory alarm can be displayed if: (a) the status of one of the first and second power sources is the fourth or fifth status; and (b) the status of the other one of the first and second power sources is the first status. Displaying the power cable disconnect and low power advisory alarm can include repeatedly flashing an indicator light for at least one second on followed by at least one second off. The indicator light can be yellow and shaped in any suitable form (e.g., diamond shaped, in the form of a battery or a battery symbol). An audio beep can be repeatedly sounded during the power cable disconnect and low power advisory alarm once every four or more seconds or until silenced via a user selection.

Outputting the combined power source alarm can include displaying a power cable disconnect and low power hazard alarm. For example, the power cable disconnect and low power hazard alarm can be displayed if: (a) the status at least one of the first and second power sources is the fourth or fifth status; (b) the status of each of the first and second power sources is the second, third, fourth, or fifth status; and (c) the status of each of the first and second power sources is not equal to the fifth status. Displaying the power cable disconnect and low power hazard alarm can include repeatedly flashing an indicator light for at least 0.25 seconds on followed by at least 0.25 seconds off. The indicator light can be red and shaped in any suitable form (e.g., diamond shaped, in the form of a battery or a battery symbol). A continuous audio tone can be sounded for a length of the power cable disconnect and low power hazard alarm or until the continuous audio tone is silenced via a user selection. The continuous audio tone can be sounded a second time after being silenced via the user selection if the power cable disconnect and low power hazard alarm persists longer than a predetermined amount of time after the audio tone is silenced.

Outputting the combined power source alarm can include displaying a no external power and power cable disconnect alarm. For example, the no external power and power cable disconnect alarm can be displayed if the status of each of the first and second power sources is equal to the fifth status. Displaying the no external power and power cable disconnect alarm can include repeatedly flashing an indicator light for at least 0.25 seconds on followed by at least 0.25 seconds off. The indicator light can be red and shaped in any suitable form (e.g., diamond shaped, in the form of a battery or a battery symbol). A continuous audio tone can be sounded for a length of the no external power and power cable disconnect alarm or until the continuous audio tone is silenced via a user selection. The continuous audio tone can be sounded a second time after being silenced via the user selection if the no external power and power cable disconnect alarm persists longer than a predetermined amount of time after the audio tone is silenced.

In another aspect, a MAC system is provided. The MAC system includes an implantable blood pump and a controller unit communicatively coupled to the blood pump. The control unit includes one or more processors and a tangible memory storing non-transitory instructions that, when executed by the one or more processors, cause the one or more processors to accomplish any of the applicable methods described herein.

BRIEF DESCRIPTION OF THE DRAWINGS

FIG. 10 illustrates combined power alarms that can be output for respective combinations of faults for individual power sources of an implantable blood pump, in accordance with many embodiments.

FIG. 11 schematically illustrates control units of a mechanically assisted circulation system, in accordance with many embodiments.

DETAILED DESCRIPTION

Figure 1:
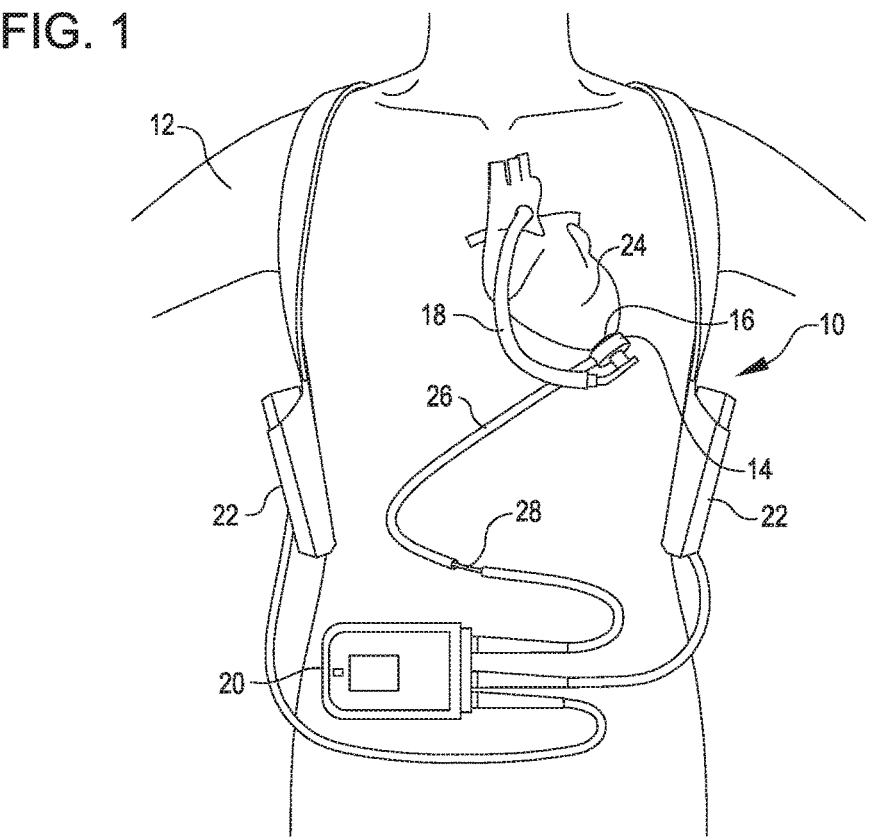
FIG. 1 is an illustration of a mechanical circulatory support system implanted in a patient's body.
Figure 2:
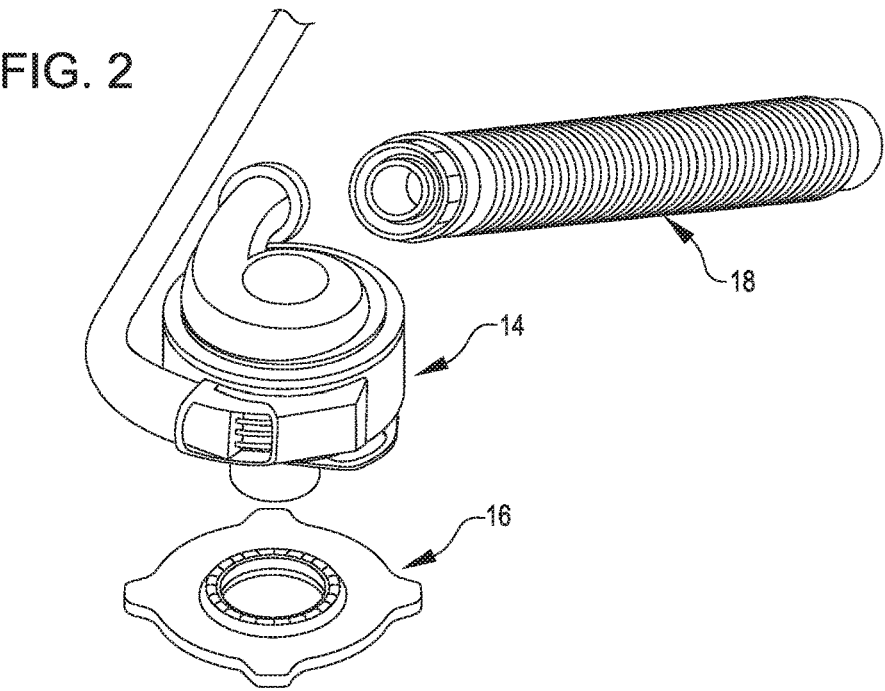
FIG. 2 is an exploded view of certain components of the circulatory support system that are implanted in a patient's body.

FIG. 1 is an illustration of a mechanical circulatory support system 10 implanted in a patient's body 12. The mechanical circulatory support system 10 comprises a implantable blood pump assembly 14, ventricular cuff 16, outflow cannula 18, an external system controller 20, and power sources 22. The implantable blood pump assembly 14 may comprise a VAD that is attached to an apex of the left ventricle, as illustrated, or the right ventricle, or both ventricles of the heart 24. The VAD may comprise a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. With reference to FIGS. 1 and 2, the blood pump assembly 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during battery 22 powered operation. A driveline 26 that exits through the patient's abdomen 28, connects the implanted blood pump assembly 14 to the external system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733, EP 1812094, and U.S. Patent Publication Nos. 2005/0071001 and 2013/0314047, all of which are incorporated herein by reference for all purposes in their entirety. The system may be powered by either one, two, or more batteries 22. It will be appreciated that although the system controller 20 and power source 22 are illustrated outside/external to the patient body, the driveline 26, system controller 20 and/or power source 22 may be partially or fully implantable within the patient, as separate components or integrated with the blood pump assembly 14. Examples of such modifications are further described in U.S. Pat. No. 8,562,508 and U.S. Patent Publication No. 2013/0127253, all of which are incorporated herein by reference for all purposes in their entirety.

Figure 3:
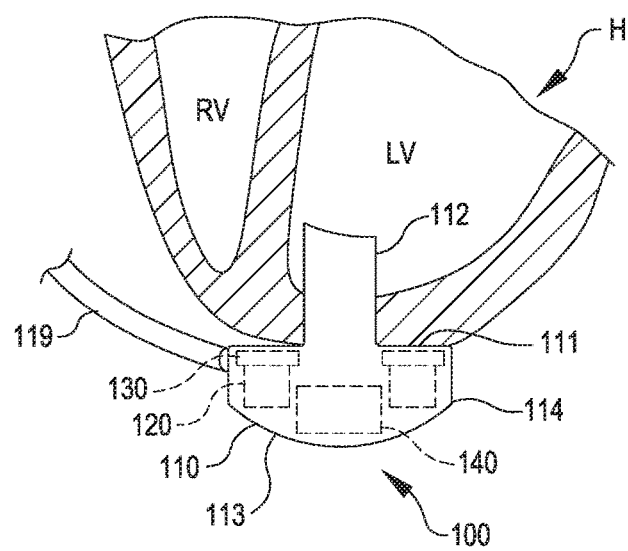
FIG. 3 is an illustration of a blood pump in an operational position implanted in a patient's body.
Figure 4:
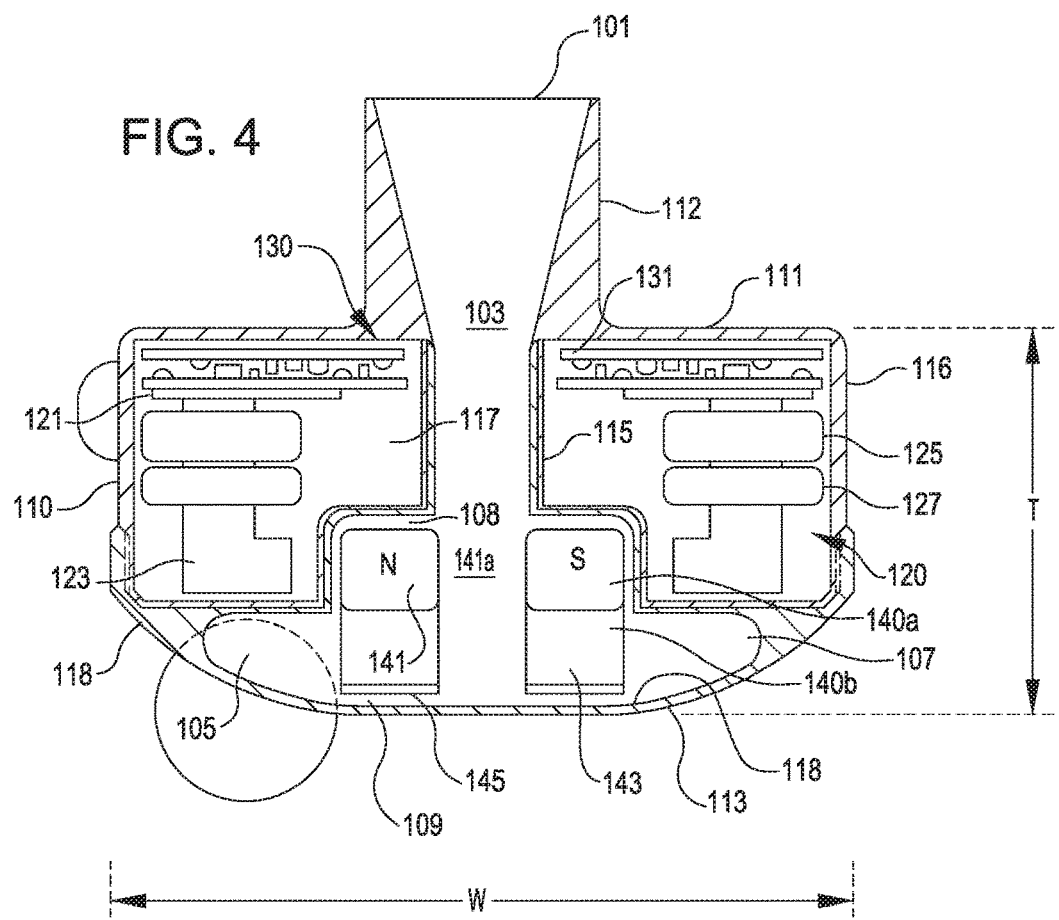
FIG. 4 is a cross-sectional view of the blood pump of FIG. 3.
Figure 5:
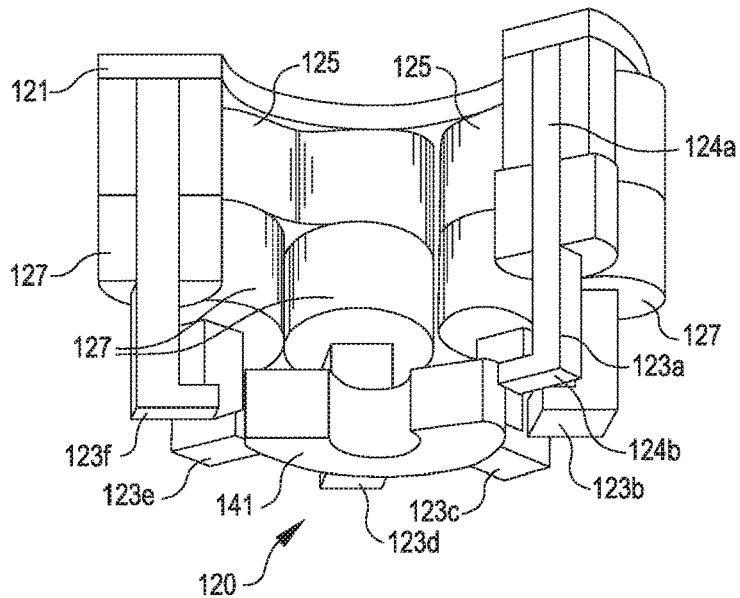
FIG. 5 is a partial cut-away perspective view of a stator of a blood pump.

With reference to FIGS. 3 to 5, a left ventricular assist blood pump assembly 100 having a circular shaped housing 110 is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump assembly 100, such as the patient's diaphragm. To construct the illustrated shape of the puck-shaped housing 110 in a compact form, a stator 120 and electronics 130 of the pump assembly 100 are positioned on the inflow side of the housing toward first face 111, and a rotor 140 of the pump assembly 100 is positioned along the second face 113. This positioning of the stator 120, electronics 130, and rotor 140 permits the edge 114 to be chamfered along the contour of the rotor 140, as illustrated in at least FIGS. 2-4, for example.

Referring to FIG. 4, the blood pump assembly 100 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadedly engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components carried on the circuit boards 131 to control the operation of the pump 100 (e.g., magnetic levitation and/or drive of the rotor) by controlling the electrical supply to the stator 120. The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

With continued reference to FIGS. 4 and 5, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a may also have a second leg 124b that extends from the first leg 124a through an opening of a circuit board 131 towards the dividing wall 115 proximate the location of the permanent magnet 141 of the rotor 140. In an aspect, each of the second legs 124b of the pole pieces 123a-123f is sticking through an opening of the circuit board 131. In an aspect, each of the first legs 124a of the pole pieces 123a-123f is sticking through an opening of the circuit board 131. In an aspect, the openings of the circuit board are enclosing the first legs 124a of the pole pieces 123a-123f.

In a general aspect, the implantable blood pump 100 may include a Hall sensor that may provide an output voltage, which is directly proportional to a strength of a magnetic field that is located in between at least one of the pole pieces 123a-123f and the permanent magnet 141, and the output voltage may provide feedback to the control electronics 130 of the pump 100 to determine if the rotor 140 and/or the permanent magnet 141 is not at its intended position for the operation of the pump 100. For example, a position of the rotor 140 and/or the permanent magnet 141 may be adjusted, e.g., the rotor 140 or the permanent magnet 141 may be pushed or pulled towards a center of the blood flow conduit 103 or towards a center of the stator 120.

Each of the pole pieces 123a-123f also has a levitation coil 127 for generating an electromagnetic field to control the radial position of the rotor 140. Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference for all purposes. The control electronics 130 and the stator 120 receive electrical power from a remote power supply via a cable 119 (FIG. 3). Further related patents, namely U.S. Pat. Nos. 5,708,346, 6,053,705, 6,100,618, 6,222,290, 6,249,067, 6,278,251, 6,351,048, 6,355,998, 6,634,224, 6,879,074, and 7,112,903, all of which are incorporated herein by reference for all purposes in their entirety.

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 is approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. The gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the pump 100. As a result of the size of the gaps 108 and 109 limiting pressure forces on the blood cells, the gaps 108 and 109 are too large to provide a meaningful hydrodynamic suspension effect. That is to say, the blood does not act as a bearing within the gaps 108 and 109, and the rotor is only magnetically-levitated. In various embodiments, the gaps 108 and 109 are sized and dimensioned so the blood flowing through the gaps forms a film that provides a hydrodynamic suspension effect. In this manner, the rotor can be suspended by magnetic forces, hydrodynamic forces, or both.

Because the rotor 140 is radially suspended by active control of the levitation coils 127 as discussed above, and because the rotor 140 is axially suspended by passive interaction of the permanent magnet 141 and the stator 120, no rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. For example, the Hall sensor may sense a current position of the rotor 140 and/or the permanent magnet 141, wherein the output voltage of the Hall sensor may be used to selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105, which may be coupled to an outflow cannula.

Figure 6:
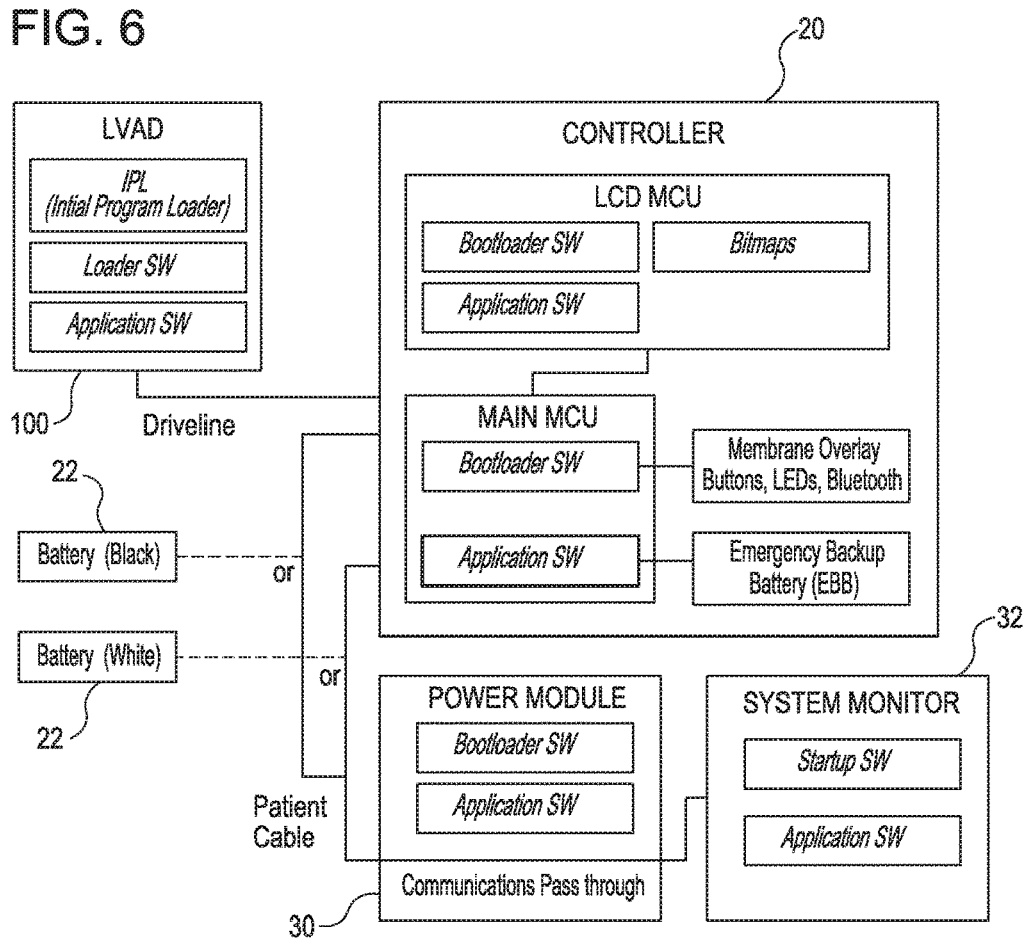
FIG. 6 is a schematic diagram of an overall communication architecture of the mechanical support system of FIG. 1.

FIG. 6 is a schematic diagram of an overall communication architecture of the mechanical support system of FIG. 1. A driveline couples the implanted blood pump assembly 100 to the external system controller 20, which monitors system operation via various software applications. The blood pump assembly 100 itself also includes several software applications that are executable by the on board electronics 130 (e.g., processors) for various functions, such as to control radial levitation and/or drive of the rotor of the pump assembly 100 during operation. The external system controller 20 may in turn be coupled to batteries 22 or a power module 30 that connect to an AC electrical outlet. The external system controller 20 may also include an emergency backup battery (EBB) to power the system (e.g., when the batteries 22 are depleted) and a membrane overlay, including Bluetooth capabilities for wireless data communication. An external computer having a system monitor 32 that is configurable by an operator, such as clinician or patient, may further be coupled to the circulatory support system for configuring the external system controller 20, implanted blood pump assembly 100, and/or patient specific parameters, updating software on the external system controller 20 and/or implanted blood pump assembly 100, monitoring system operation, and/or as a conduit for system inputs or outputs.

Combined Power Source Alarms

Due to the critical nature of the assistance provided to a patient by a MAC system, typical MAC systems include redundant power supplies. For example, the mechanical circulatory support system 10 includes two power sources 22. The reservoir of power residing in the two power supplies 22 available to power the mechanical circulatory support system 10 depends on state of charge of both of the power sources 22. Moreover, the redundant nature of the power sources 22 may reduce the criticality of faults that occur in only one of the power sources 22. Accordingly, in many embodiments, instead of outputting an alarm to the patient for each detected fault in the power sources 22, or in any other power source to the mechanical circulatory support system 10, a combined power source fault is output that appropriately reflects the combined impact of the individual faults.

Figure 7:
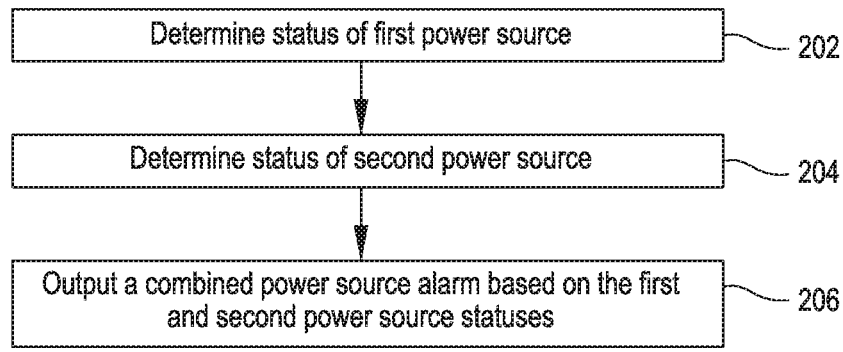
FIG. 7 is a simplified block diagram of a method for outputting a combined power source alarm for an implantable blood pump, in accordance with many embodiments.

FIG. 7 shows acts of a method 200 for outputting a combined power source alarm, in accordance with many embodiments. The method 200 includes act 202 in which the status of a first power source is determined, and act 204 in which the status of a second power source is determined. The statuses can include, for example, relative state of charge levels, whether the power source is unknown (e.g., via presenting an unrecognized voltage level), and whether the power source is disconnected (e.g., via presenting an insufficient voltage level). In act 206, a combined power source alarm, such as illustrated in FIG. 10, is outputted based on the statuses of the first and second power sources.

Figure 8:
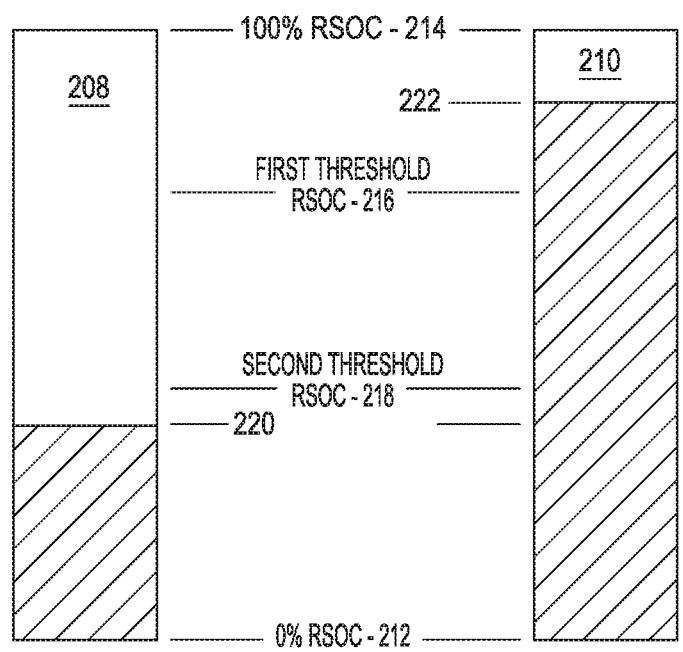
FIG. 8 illustrates relative state of charge in redundant power sources for an implantable blood pump, in accordance with many embodiments.

FIG. 8 illustrates example relative state of charge (RSOC) in redundant power sources for an implantable blood pump.

The illustrated power sources 208, 210 have respective RSOC between a zero percent RSOC 212 (i.e., empty) and a one-hundred percent RSOC 214 (i.e., full). In many embodiments, one or more intermediate thresholds levels of RSOC are established by which the RSOC in a particular power source can be characterized. For example, in the illustrated embodiment, a first threshold RSOC 216 is established below the one-hundred percent RSOC 214 and a second threshold RSOC 218 is established below the first threshold RSOC 216. The power source 208 is shown as having a relatively low RSOC 220 that is below the second threshold RSOC 218. In contrast, the power source 210 has a relatively high RSOC 222 that is above the first threshold RSOC 216. The combined power amount that the power sources 208, 210 can deliver is a result of the relatively low RSOC of the power source 208 combined with the relatively high RSOC of the power source 210. Accordingly, a combined power status alarm can be outputted that reflects that both batteries do not have the relatively high RSOC 222 and both batteries do not have the relatively low RSOC 220, but instead reflects that the combination of the two power sources 208, 210 have an effective combined RSOC inbetween the RSOC 220 and RSOC 222.

Figure 9:
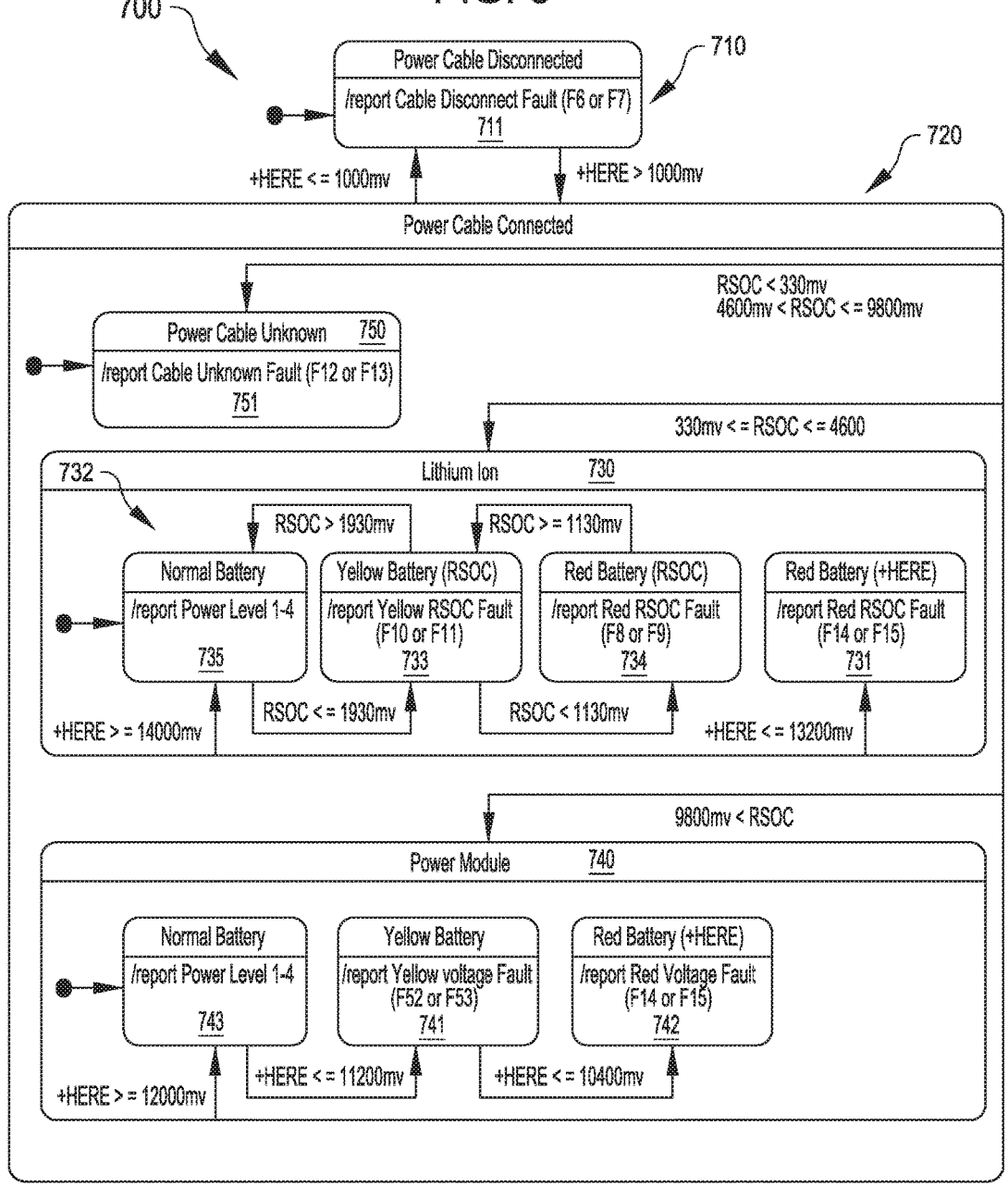
FIG. 9 illustrates fault detection in a variety of power sources for an implantable blood pump, in accordance with many embodiments.

FIG. 9 illustrates a graphical description 700 of exemplary power monitoring rules for a power monitor, which can be a software and/or hardware component of the external controller 20. The power monitor may first determine whether a cable is disconnected 710. When ADC driver returns voltage less than or equal to a disconnect voltage (e.g., 1000 mV in the illustrated embodiment), the power monitor may report a cable disconnect fault for the respective cable 711. When the ADC driver returns voltage greater than the disconnect voltage (e.g., 1000 mV), the power monitor may determine that the cable is connected 712. Once the power monitor determines that the cable is connected, the power monitor may be configured to determine the power source 720.

When the ADC driver returns an RSOC greater than or equal to a minimum battery threshold (e.g., 330 mV in the illustrated embodiment) and lower than a maximum battery threshold (e.g., 4600 mV in the illustrated embodiment), the power monitor may be configured to determine that the power source is a battery 730 (e.g., a rechargeable lithium ion battery, or the like). When the RSOC is greater than a minimum power module threshold (e.g., 9800 mV in the illustrated embodiment), the power monitor may be configured to determine that the power source is a power module 740. When the RSOC is less than the minimum battery threshold (e.g., 330 mV) or greater than the maximum battery threshold (e.g., 4600 mV) but less than or equal to the minimum power module threshold (e.g., 9800 mV), the power monitor may be configured to determine that the power source is unknown 750 and report a cable unknown fault 751.

When the power monitor determines that the power source is a battery 730, the power monitor may be configured to monitor a charge and/or voltage of the battery. When the voltage is less than or equal to a voltage red fault threshold (e.g., 13200 mV in the illustrated example for an exemplary lithium ion battery), the power monitor may be configured to report a voltage red fault status for the power cable 731. When a voltage is greater than or equal to a normal voltage threshold (e.g., 14000 mV in the illustrated example for an exemplary lithium ion battery), the power monitor may be configured to then analyze for RSOC faults of the battery 732.

For example, as illustrated in FIG. 9, when the RSOC is less than or equal to a RSOC yellow fault threshold (e.g., 1930 mV in the illustrated embodiment for a lithium ion battery), the power monitor may report a RSOC yellow fault 733. When the RSOC is less than RSOC red fault threshold (e.g., 1130 mV in the illustrated embodiment for a lithium ion battery), the power monitor may report a RSOC red fault 734. When the RSOC is greater than the RSOC yellow fault threshold (e.g., 1930 mV), the power monitor may determine that the battery is operating normally and may report a power level (e.g., 1-4) 735 to a user via a system monitor, LED power indicators, or the like.

When the power monitor determines that the power source is a power module 740, the power monitor may be configured to monitor a voltage level of the power monitor. When the voltage is less than or equal to a yellow voltage fault threshold (e.g., 11200 mV in the illustrated embodiment), the power monitor may report a yellow voltage fault 741. When the voltage is less than or equal to a red voltage fault threshold (e.g., 10400 mV in the illustrated embodiment), the power monitor may report a red voltage fault 742. When the voltage is greater than the yellow voltage fault threshold, the power monitor may determine that the power monitor is operating normally and may report a power level (e.g., 1-4) 743 to a user via a system monitor, LED power indicators, or the like.

The power monitor may report one fault per cable each time the monitor executes. Faults may remain until a lower priority fault (or no fault) occurs. For example, when going from voltage red fault to disconnected, the red alarm may remain set, but when going from disconnected to voltage red, the disconnect fault may be cleared.

FIG. 10 illustrates a chart describing exemplary alarms for various situations depending on the status of a first cable (e.g., black cable status) and a second cable (e.g., white cable status). As illustrated, a low power hazard condition is triggered when the power monitor reports an unknown, red, or yellow fault for one cable and reports a disconnected, unknown, or red fault for the other cable. When the power monitor reports cable disconnected faults for both cables (white and black), a "no external power" condition is triggered. When one of the cables is green (i.e., not reported as disconnected, unknown, red, or yellow), the system may be configured to trigger at most a low power advisory no matter the status of the other cable. Further, a low power advisory may be issued when the power monitor reports a yellow fault for both cables. When both cables have a green status, no alarms are issued.

Fault Processing for False Alarm Suppression

In many embodiments, the mechanical circulatory support system 10 incorporates a fault processing approach that suppresses the output of false alarms. The fault processing approach utilizes a progression from a detected fault condition to a related alarm. For example, a monitoring unit (e.g., a power source monitor, a LVAD monitor) reports fault conditions to a fault handler unit. A fault condition is a single instance where the monitoring unit reports a fault condition to the fault hander unit. The fault handler indicates that the fault is active after a fault condition is reported to the fault handler by the monitoring unit for a predetermined number of times. The predetermined number of times is referred to herein as a set soaking number, which can be any whole number (e.g., one or greater) representing the required number of occurrences before a particular fault is considered active. This process is referred to herein as "soaking." An alarm handler unit monitors active faults and generates an alarm when the fault (or combination of faults) has persisted long enough to warrant an alarm. The required persistence time can be any suitable amount of time including a zero amount of time. The fault processing approach is described in further detail below with respect to FIG. 11 through FIG. 13.

FIG. 11 schematically illustrates control units of a mechanically assisted circulation system, in accordance with many embodiments. The fault processing approach can be implemented using any suitable combination of the control units. Moreover, while a particular embodiment of control units is illustrated and described, the fault processing approach can be implemented using any suitable control unit, or suitable combination of suitable control units. In the illustrated embodiment, the control units include the electronics 130, the external system controller 20, and the system monitor 32.

In many embodiments, the external system controller 130 includes one or more processors 132 and a memory device 133 operatively coupled to the one or more processors 132. The memory device 133 can include any suitable forms of memory, for example, a read only memory (ROM) 134 and a random access memory (RAM) 135. The ROM 134 can be used to store basic instructional sets for the operation of the one or more processors 132. The RAM 135, or any other suitable memory device such as long term, short term, volatile, nonvolatile, or other suitable storage medium, can be used to store instructions for an LVAD monitor unit that detects and reports LVAD faults to the fault handler unit.

In the illustrated embodiment, the external system controller 20 includes one or more processors 224 and a memory device 226 operatively coupled to the one or more processors 224. The memory device 226 can include any suitable forms of memory, for example, a ROM 228 and a RAM 230. The ROM 228 can be used to store basic instructional sets for the operation of the one or more processors 230. The RAM 230, or any other suitable memory device such as long term, short term, volatile, nonvolatile, or other suitable storage medium, can be used to: (a) store instructions for a power monitor unit that detects and reports power source faults to the fault handler unit; (b) store instructions for the fault handler unit; and (c) store instructions for the alarm handler unit.

In the illustrated embodiment, the system monitor 32 includes one or more processors 232 and a memory device 234 operatively coupled to the one or more processors 232. The memory device 234 can include any suitable forms of memory, for example, a ROM 236 and a RAM 238. The ROM 236 can be used to store basic instructional sets for the operation of the one or more processors 230. The RAM 230, or any other suitable memory device such as long term, short term, volatile, nonvolatile, or other suitable storage medium, can be used to store instructions providing for the functionality of the system monitor 32 as describe herein.

In the illustrated embodiment, the LVAD electronics 130 communicates with the external system controller 20 via a communication line 240. While any suitable means of communication can be used to communicate between the electronics 130 and the external system controller 20, including any suitable wireless communication, the communication line 240 can be a suitable serial communication line. In a similar manner, the system monitor 32 communicates with the external system controller 20 via a communication line 242. While any suitable means of communication can be used to communicate between the system monitor 32 and the external system controller 20, including any suitable wireless communication, the communication line 242 can be a suitable serial communication line.

Figure 12:
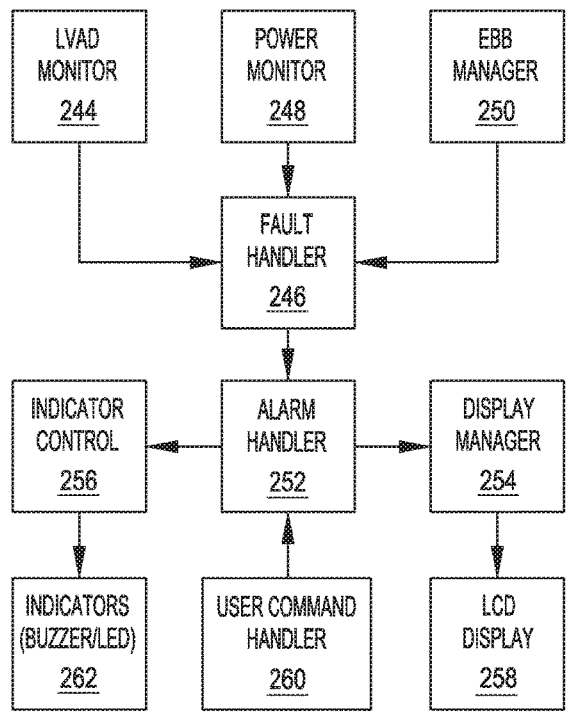
FIG. 12 schematically illustrates control modules and output devices in a mechanically assisted circulation system that are used to generate an alarm based on fault detections, in accordance with many embodiments.

FIG. 12 schematically illustrates control modules and output devices in a mechanically assisted circulation system that are used to generate an alarm based on fault detections, in accordance with many embodiments. The illustrated control modules can be implemented on any suitable controller, including any suitable one or combination of the control units illustrated in FIG. 11. Each of the illustrated control modules can be impleted as a software module, via hardware, or any suitable combination of software and hardware.

In the illustrated embodiment, the control modules include an LVAD/VAD monitor 244. The LVAD monitor 244 is configured to detect faults in the left ventricular assist blood pump assembly 100 and report the detected faults to a fault handler 246. In many embodiments, the faults reported by the LVAD monitor 244 to the fault handler 246 include: (a) low flow; (b) pump stopped; (c) low speed hazard; (d) low speed advisory; (e) a pulsatile (suction) event; (f) excessive rotor displacement and/or noise; (g) circuit over temperature; (h) reference voltage fault; (i) bearing A over current; (j) bearing B over current; (k) drive A over current; (l) drive B over current; (m) EEPROM communication error; (n) operating data corruption; (o) magnetic centering fault; (p) harmonic compensation fault; and (q) rotor displacement fault. The LVAD monitor 244 can be implemented in the LVAD electronics 130.

The illustrated control modules include a power monitor 248. The power monitor 248 is configured to: (a) detect relative state of charge (RSOC) battery levels; and (b) detect faults in the power supply system for the mechanical circulatory support system 10 and report the detected faults to a fault handler 246. The power monitor 248 periodically checks the voltages on the white and black power cables to: (a) gather RSOC status on the white and black power cables; (b) gather non-RSOC status on the white and black power cables; (c) determine the type of power source connected; and (d) calculate battery gauge information. After determining the status, the power monitor 248 sets and clears faults related to the voltage levels on each power cable. The following faults are reported to the fault handler 246 by the power monitor 248: (a) white cable disconnected fault; (b) black cable disconnected fault; (c) white cable RSOC red fault; (d) black cable RSOC red fault; (e) white cable RSOC yellow fault; (f) black cable RSOC yellow fault; (g) white cable unknown fault; (h) black cable unknown fault; (i) white cable voltage red fault; and (j) black cable voltage red fault.

The illustrated control modules include an emergency backup battery (EBB) manager 250. In many embodiments, the faults reported by the EBB manager 250 to the fault handler 246 include: (a) the EBB usage duration exceeds the usage duration limit; (b) the current date exceeds the expiration date for the EBB; (c) the current date exceeds the used by date (calculated by adding shelf life to last top off date); (d) an EBB memory tag fault; (e) communication with the EEPROM has failed; (f) the EBB has failed to completely charge within 4 hours and the bus voltage is greater than 13.0 Volts; and (g) the EBB is currently in use.

The fault handler 246 contributes to alarm management. The fault handler 246 provides a centralized data store for all fault attributes information. The fault handler 246 accepts reports of fault conditions from other application level units; manages soaking thresholds used to determine when a fault condition becomes classified as active, cleared, or unknown; provides fault information to the other units; and reports fault change events to an event logger. The fault handler processes reported fault conditions to determine when a fault flag should be set or cleared.

The illustrated control modules include an alarm handler 252. The alarm handler 252 The alarm handler 252 monitors faults reported by the fault handler 246 and initiates an alarm response when the fault (or combination of faults) has persisted long enough to be considered an alarm. The alarm handler 252 provides the following functionality: (a) periodically monitors fault data and fault persistence information to determine which alarms should be raised based on alarm policy and system mode; (b) controls system response when an alarm has been detected; (c) maintains alarm duration for each alarm; (d) keeps recent alarm history to be queried by a display manager 254, which can be a software and/or hardware component of the external controller 20; (e) manages silencing of alarms; (f) prioritizes alarms and alarm responses; (g) uses an indicator unit 256 (which can be a software and/or hardware component of the external controller 20) to control audio and LED response to alarms; (h) determines the alarms to be presented to user based on system mode; (i) provide the display manager unit 254 information as what alarm message should be displayed on LCD screen; (j) provides an interface for other units to query alarm related status; (k) notifies an event logger when an alarm changes; (l) cancels functional test when a new alarm becomes active; and (m) updates fault durations. The display manager 254 manages the information displayed on an LCD 258, which in many embodiments is a component of the external controller 20. The indicator control 256 provides control over indicators 262 (e.g., buzzer(s) and LED(s)), which in many embodiments are components of the external controller 20. A user command handler 260, which in many embodiments is a software and/or hardware component of the external controller 20, transmits user commands, such as alarm silencing input, to the alarm handler 252.

Figure 13:
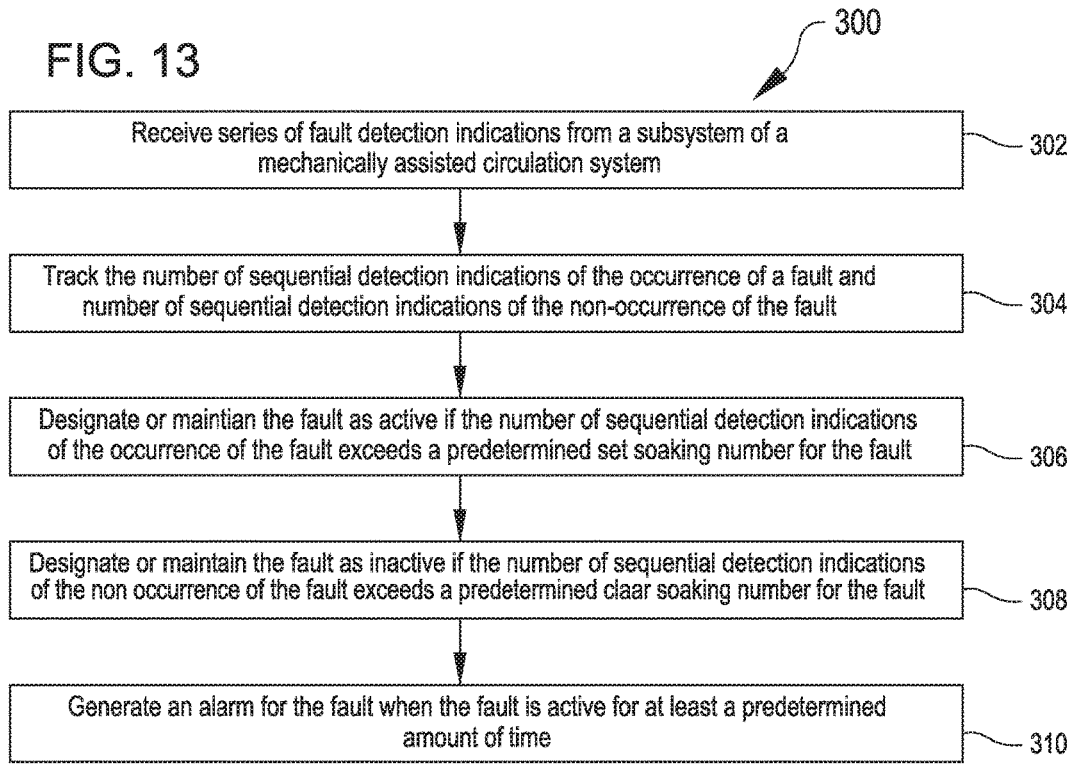
FIG. 13 is a simplified block diagram of a method for generating an alarm based on fault detections in a mechanically assisted circulation system, in accordance with many embodiments.

FIG. 13 shows acts of a method 300 for generating an alarm based on fault detections in a mechanically assisted circulation system, in accordance with many embodiments. The method 300 can be practiced in any suitable mechanically assisted circulation system, including the mechanically assisted circulation systems described herein.

The method 300 includes receiving a series of fault detection indications from a subsystem of a mechanically assisted circulation system (act 302). For example, as described herein, the LVAD monitor 244 can transmit the series of fault detections for any one of the described LVAD faults reported by the LVAD monitor 244 to the fault handler 246. As another example, the power monitor 248 can transmit the series of fault detections for any one of the described faults reported by the power monitor 248 to the fault handler 246.

In act 304, the number of sequential detection indications of the occurrence of a fault are tracked and the number of sequential detection indications of the non-occurrence of a fault are tracked. For example, the fault hander 246 can use the number of sequential detection indications of the occurrence of a fault to determine if the fault should be considered to be active based on whether the number of sequential indications of the occurrence of the fault exceeds a predetermined set soaking number for the particular fault. The fault handler can use the number of sequential detection indications of the non-occurrent of the fault to determine if the fault should be considered to be non-active based on whether the number of sequential indications of the non-occurrence of the fault exceeds a predetermined clear soaking number for the particular fault. The determination of whether the fault is active or inactive is based on a subseries of the indications disposed at the end of the series of indications. Accordingly, the status of the fault can only be one of active or inactive at any particular point in time.

In act 306, the fault is designated or maintained as active if the number of sequential detection indications of the occurrence of the fault exceeds the predetermined set soaking number for the fault. In act 308, the fault is designated or maintained as inactive if the number of sequential detections indications of the non-occurrence of the fault exceeds the predetermined clear soaking number for the fault. In act 310, an alarm is generated for the fault when the fault is active form at least a predetermined amount of time.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of generating an alarm in a mechanically assisted circulation (MAC) system, the method comprising:
   monitoring a subsystem of the MAC system, by a subsystem monitor module, to detect a fault condition of the subsystem;
   generating, by the subsystem monitor module, a series of indications for the fault condition indicative of whether the fault condition is detected during a respective time period;
   processing the series of indications, by a fault handler module, to generate a fault status output indicative of whether the fault condition is classified as being active, the fault handler module classifying the fault condition as active if each of a first subseries of the series of indications at the end of the series of indications indicate detection of the fault condition, the first subseries including a predetermined set soaking number of the series of indications, the set soaking number being at least two; and
   outputting an alarm for the fault condition in response to the fault condition being reclassified as active by the fault handler module.

2. The method of claim 1, wherein the set soaking number is from three to ten.

3. The method of claim 1, wherein:
   the subsystem comprises a blood pump assembly; and
   the fault condition comprises a fault condition of the blood pump assembly.

4. The method of claim 3, wherein the fault condition comprises one of:
   a low flow fault condition;
   a pump stopped fault condition;
   a low speed hazard fault condition; and
   a low speed advisory fault condition.

5. The method of claim 3, wherein the fault condition comprises a suction event fault condition.

6. The method of claim 3, wherein the fault condition comprises one of:
   excessive rotor displacement fault condition;
   excessive rotor noise fault condition;

a magnetic centering fault condition;
a harmonic compensation fault condition; and
a displacement fault condition.

7. The method of claim 3, wherein the fault condition comprises a circuit over temperature fault condition.

8. The method of claim 3, wherein the fault condition comprises one of:
a magnetic bearing over current fault condition; and
a drive coil over current fault condition.

9. The method of claim 1, wherein:
the subsystem comprises a battery power supply system; and
the fault condition comprises a fault condition of the battery power supply system.

10. The method of claim 9, wherein the fault condition comprises one of:
a battery cable disconnect fault condition;
a battery relative state of charge fault condition;
a battery voltage level fault condition; and
an unknown power source fault condition.

11. The method of claim 1, wherein:
the subsystem comprises an emergency backup battery (EBB); and
the fault condition comprises a fault condition of the blood pump assembly.

12. The method of claim 11, wherein the fault condition comprises one of:
usage duration of the EBB exceeding a usage duration limit fault condition;
an expiration date for the EBB has passed fault condition;
a memory tag fault condition;
a communication fault condition;
a charge failure fault condition; and
the EBB being used to power the MAC system fault condition.

13. The method of claim 1, wherein the fault conditions is classified as being active or inactive at any particular time.

14. The method of claim 1, wherein outputting the alarm for the fault condition comprises generating the alarm for the fault condition, by an alarm handler module, in response to the fault status output indicating, for a persistence time between one and fifteen seconds, that the fault condition is classified as active.

15. The method of claim 1, wherein the fault handler module classifies the fault condition as inactive if each of a second subseries of the series of indications at the end of the series of indications indicate non-detection of the fault condition, the second subseries including a predetermined clear soaking number of the series of indications.

16. The method of claim 15, wherein the clear soaking number is from one to three.

17. The method of claim 15, wherein the clear soaking number is equal to or greater than the set soaking number.

18. A method of generating an alarm in a mechanically assisted circulation (MAC) system, the method comprising:
monitoring a subsystem of the MAC system, by a subsystem monitor module, to detect a fault condition of the subsystem;
generating, by the subsystem monitor module, a series of indications indicative of whether the fault condition is detected by the subsystem monitor module;
processing the series of indications, by a fault handler module, to generate a fault status output indicative of whether the fault condition is classified as being active, the fault handler module classifying the fault condition as active if each of a first subseries of the series of indications at the end of the series of indications indicate detection of the fault condition, the first subseries including a predetermined set soaking number of the series of indications; and
outputting an alarm for the fault condition in response to the fault condition being classified as active for a persistence time between one and fifteen seconds.

19. The method of claim 18, wherein the fault handler module classifies the fault condition as inactive if each of a second subseries of the series of indications at the end of the series of indications indicate non-detection of the fault condition, the second subseries including a predetermined clear soaking number of the series of indications.

20. The method of claim 19, further comprising clearing the alarm in response to the fault condition be reclassified from active to inactive.

* * * * *